(12) United States Patent
Dal Molin et al.

(10) Patent No.: US 8,050,749 B2
(45) Date of Patent: *Nov. 1, 2011

(54) RECONSTRUCTION OF A SURFACE ELECTROCARDIOGRAM BASED UPON AN ENDOCARDIAL ELECTROGRAM

(75) Inventors: Renzo Dal Molin, Chatillon (FR); Anissa Bourguiba, rue Saint Jacques (FR); Fabienne Porée, Rennes (FR); Guy Carrault, Cesson sevigné (FR); Alfredo Hernandez, Rennes (FR)

(73) Assignee: ELA Medical S.A.S., Montrouge (FR)

( * ) Notice: Subject to any disclaimer, the term of this patent is extended or adjusted under 35 U.S.C. 154(b) by 499 days.

This patent is subject to a terminal disclaimer.

(21) Appl. No.: 11/861,106

(22) Filed: Sep. 25, 2007

(65) Prior Publication Data
US 2008/0114259 A1    May 15, 2008

(30) Foreign Application Priority Data
Sep. 25, 2006 (FR) .................................. 06 08367

(51) Int. Cl.
*A61B 5/0402* (2006.01)
(52) U.S. Cl. .......................... 600/509; 600/512
(58) Field of Classification Search ............ 600/512, 600/509, 523, 510
See application file for complete search history.

(56) References Cited

U.S. PATENT DOCUMENTS

| | | | | |
|---|---|---|---|---|
| 4,949,725 A * | 8/1990 | Raviv et al. | ............... | 600/544 |
| 5,305,745 A * | 4/1994 | Zacouto | ............... | 600/324 |
| 5,740,811 A * | 4/1998 | Hedberg et al. | ............... | 600/510 |
| 5,827,195 A | 10/1998 | Lander | | |
| 6,658,283 B1 * | 12/2003 | Bornzin et al. | ............... | 600/510 |
| 6,766,190 B2 | 7/2004 | Ferek-Petric | | |
| 6,772,004 B2 * | 8/2004 | Rudy | ............... | 600/509 |
| 6,839,588 B1 * | 1/2005 | Rudy | ............... | 600/523 |
| 6,975,900 B2 * | 12/2005 | Rudy et al. | ............... | 600/523 |
| 6,980,850 B1 | 12/2005 | Kroll et al. | | |
| 2003/0083587 A1 * | 5/2003 | Ferek-Petric | ............... | 600/512 |
| 2005/0197674 A1 | 9/2005 | McCabe et al. | | |
| 2005/0288600 A1 | 12/2005 | Zhang et al. | | |

OTHER PUBLICATIONS

Lian et al.; Synthesizing Surface ECGs from Intracardiac Electrograms Using an Adaptive Filter Method; Computers in Cartiology 2007; 34:537-540.*
Pang et al.; Automatic Identification of Cardiac Activations in the Multi-Channel Intracardiac ECGs; IET Conference Proceedings Jul. 2006.*
Hinrikus et al.; Correlation Between Masured Surface and Endocardial Electrical Signals of Heart; 2nd International Conference on Bioelectromagnetism; Feb. 1998; Melbourne Australia.*

(Continued)

*Primary Examiner* — Carl H Layno
*Assistant Examiner* — Paula J Stice
(74) *Attorney, Agent, or Firm* — Orrick Herrington & Sutcliffe, LLP

(57) ABSTRACT

The reconstruction of a surface electrocardiogram based upon an endocardial electrogram. This method includes: (a) acquisition (10) of a plurality of endocardial electrogram signals (EGM) through a plurality of endocardial leads defined based upon endocardial electrodes; (b) calculation (12), by combining the endocardial electrogram (EGM) signals acquired at step (a), of the corresponding endocardial vectogram (VGM); (c) angular rescaling (14) of the orthonormalized mark of the endocardial vectogram (VGM) with that of the surface vectocardiogram (VCG); (d) estimation (16), based upon the endocardial vectogram (VGM) calculated at step (b), of a reconstructed surface vectocardiogram (VCGreconstructed), and (e) calculation (18) of the surface electrocardiogram (ECG) corresponding to said reconstructed surface vectocardiogram (VCGreconstructed).

28 Claims, 5 Drawing Sheets

OTHER PUBLICATIONS

Gu et al.; Analysis of Vector-ECG and Magneto-ECG based MCG data; Proceedings of NFSI & ICFBI 2007; Hangzou, China; Oct. 12-14, 2007.*

Gulrajani et al.; The forward problem of electrocardiography: from heart models to body surface potentials; Proceedings of the 19th International Conference; IEEE/EMBS; Oct. 30-Nov. 2, 1997; Chicago IL.*

"Usefulness of three additional electrocarthographic chest leads (V7, V8 and V9) in the diagnosis of acute myocardial infarction," Libardo J. Melendez, et al., CMA Journal/Oct. 7, 1978/vol. 119, pp. 745-748.

"Surface ECG reconstruction from intracardiac EGM: a PCA-vectocardiogram method," A. Kachenoura, et al., Signals, Systems and Computers, 2007. ACSSC 2007, Conference Record of the Forty-First Asilomar Conference on.

Office Action dated Oct. 29, 2010 for U.S. Appl. No. 11/935,334.

* cited by examiner

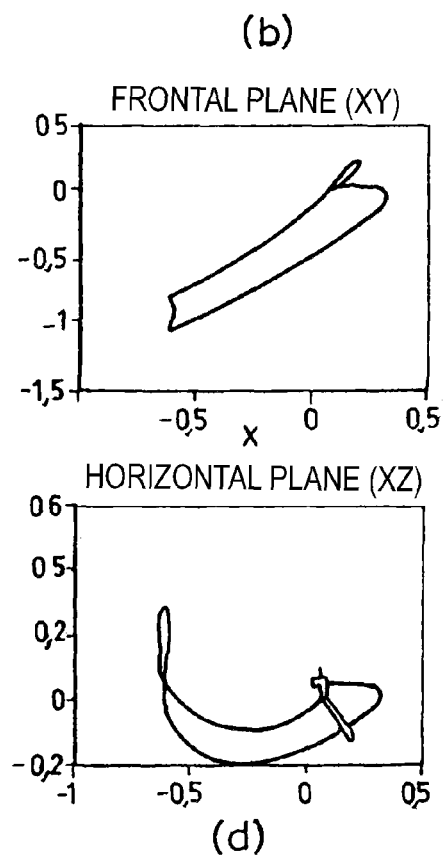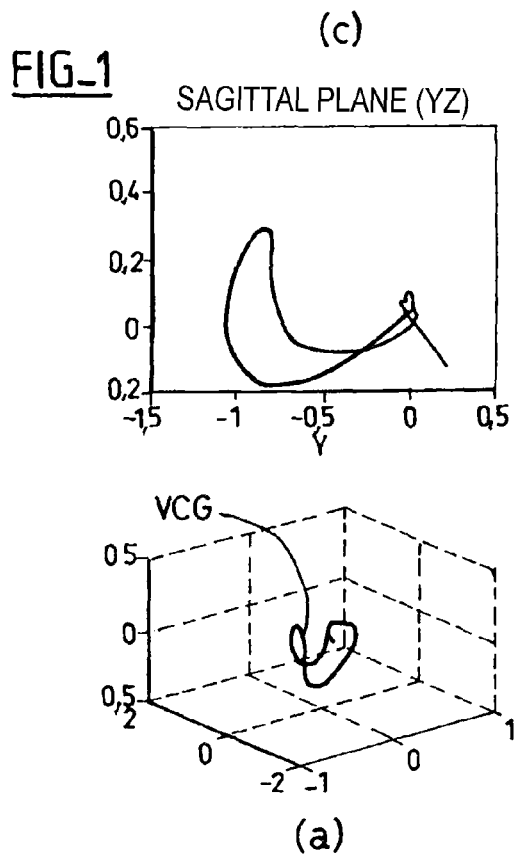
FIG_1
(b) FRONTAL PLANE (XY)
(c) SAGITTAL PLANE (YZ)
(d) HORIZONTAL PLANE (XZ)
(a) VCG
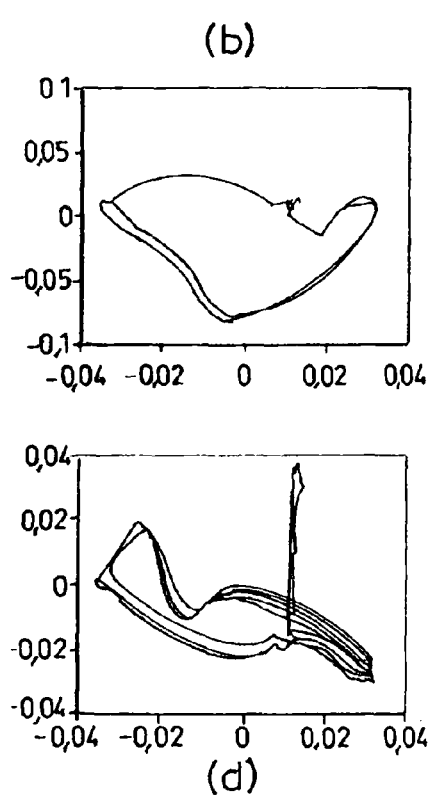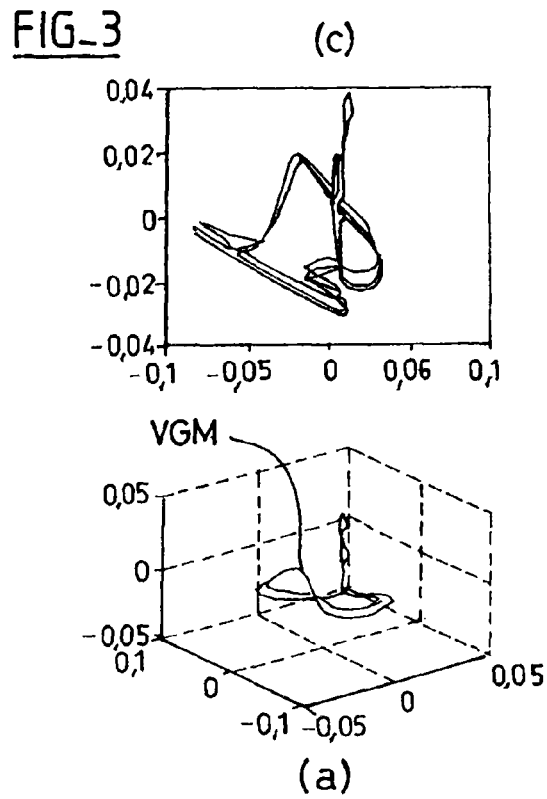
FIG_3
(a) VGM

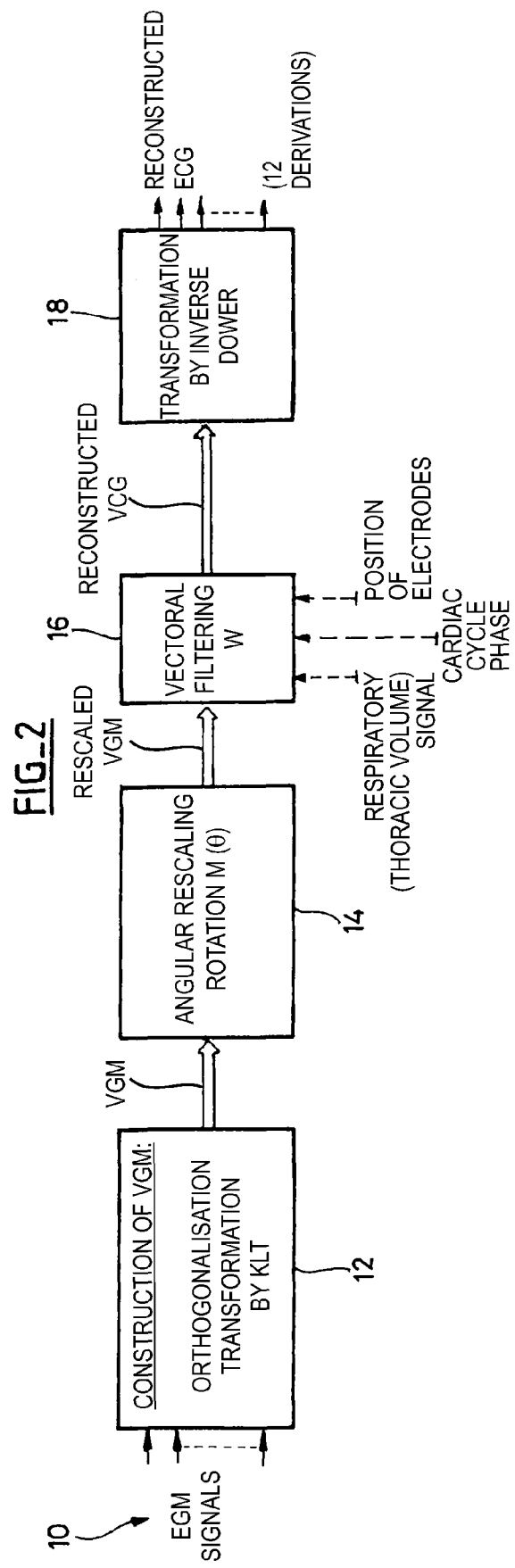

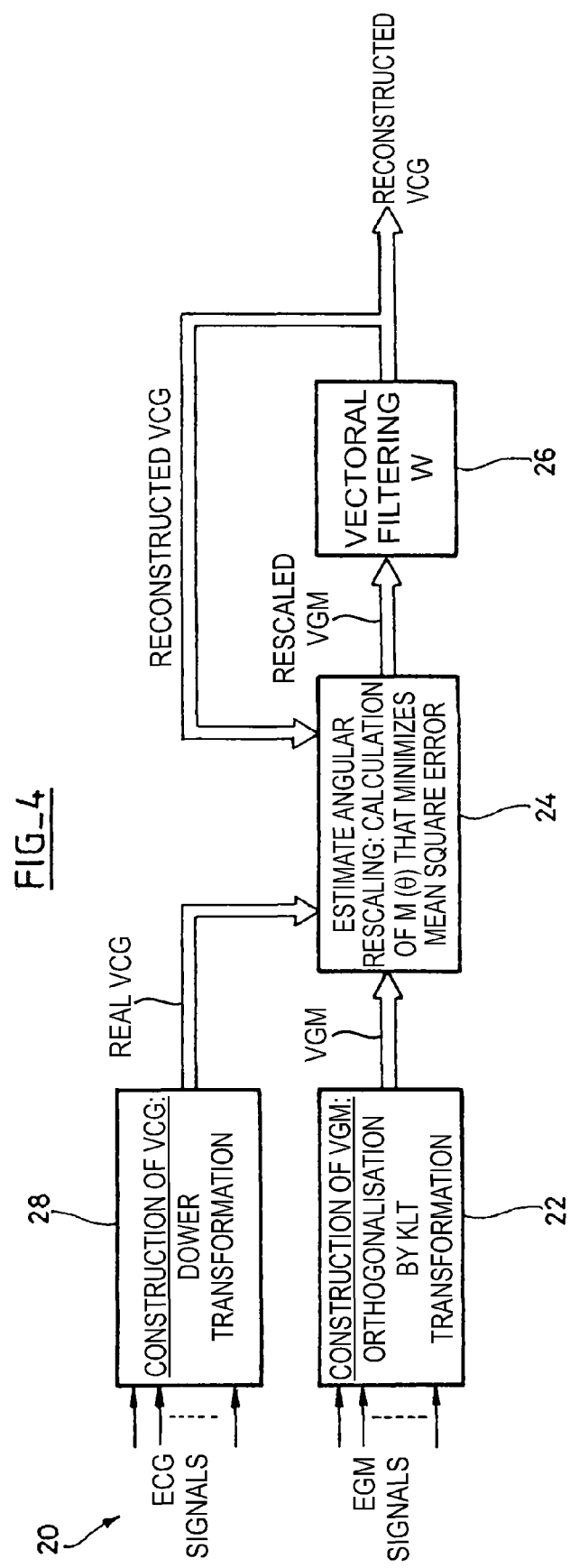

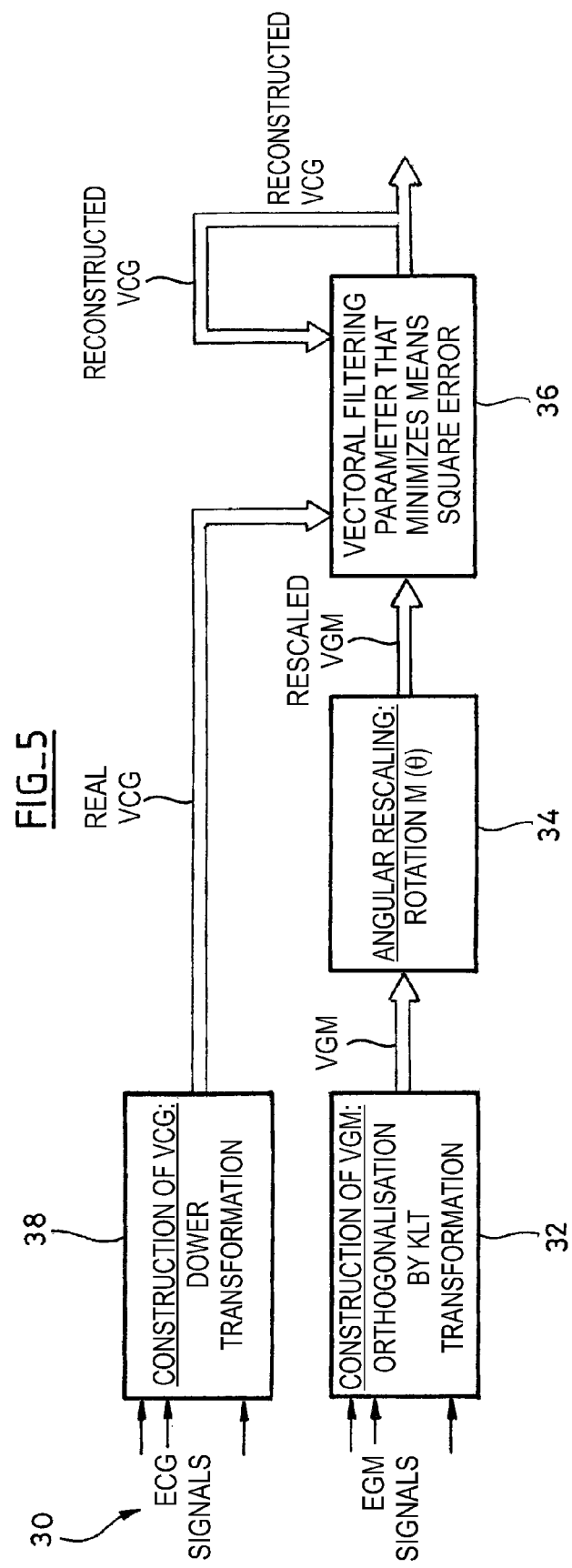

RECONSTRUCTION OF A SURFACE ELECTROCARDIOGRAM BASED UPON AN ENDOCARDIAL ELECTROGRAM

FIELD OF THE INVENTION

The present invention relates to "active implantable medical devices" as such devices are defined by the Jun. 20, 1990 Directive 90/385/CEE of the Council of the European Community, and particularly to the implantable devices that continuously monitor the cardiac rhythm and deliver to the heart, when necessary, electrical pulses for pacing, resynchronization, cardioversion and/or defibrillation in the case of a rhythm disorder that is detected by such device. The invention more particularly relates to processing the signals representative of cardiac depolarization potentials of the myocardium, such signals being collected through epicardial or endocardial electrodes for pacing, sensing or defibrillation of the atria or right and left ventricles, of these implantable devices. Even more particularly, the present invention is directed to a method for the reconstruction of a surface electrocardiogram (ECG) starting from an endocardial or epicardial electrogram (EGM).

BACKGROUND OF THE INVENTION

It is known that EGM signals can be collected by use of electrodes placed on endocardial or epicardial leads that are implanted with the device. These signals, directly correlated to the electrical activity of cardiac cells, provide much useful information for the purpose of assessing the patient's condition. Hence, after amplifying, digitizing and filtering, they are mainly utilized to control the cardiac pacer and diagnose some rhythm disorders requiring, for example, automatic triggering of an antitachycardia, antibradicardia, or interventricular resynchronization therapy, through implementing advanced analysis and decision taking algorithms.

However, when it comes to analyzing the heart rhythm in a subjective way, in order to perform a diagnostic or readjust the parameters of an implanted device, the order to perform a diagnostic or readjust the parameters of an implanted device, the practitioners prefer, in practice, to interpret the information given by the surface electrocardiogram (ECG). An ECG allows one to visualize in a direct manner, a certain number of determining factors (QRS width, etc.) and thereby weigh the evolution of a heart failure.

Indeed, the ECG and EGM signals, though they actually have the same source (the electrical activity of myocardium), visually appear in much different manners: the EGM collected by the implantable device provides local information on the electrical activity of a group of heart cells, whereas the ECG appears in the form of more global information, influenced by the propagation of the electrical signal between the myocardium and body surface, and by a certain number of morphologic and pathological specificities. Thus, the display of EGM signals is not very useful to a practitioner who is used to interpreting surface ECG signals.

It is also usually the ECG signals that are recorded over a long period of time through ambulatory practice by Holter recorders, so as to be further processed and analyzed in order to evaluate the clinical condition of the patient and eventually diagnose whether a heart rhythm disorder is present.

Hence, when a patient implanted with a medical device comes to his practitioner for a routine visit, the practitioner uses two distinct devices: an ECG recorder and an external implant programmer. In order to collect the ECG signal, the practitioner places a certain number of electrodes on the patient's torso, so as to define the usual twelve useful leads corresponding to as many distinct ECG signals. As to the external programmer, it is used to control certain operating parameters of the implantable device (for example, the battery life), download data from the implantable device memory, and eventually to modify the parameters thereof, or upload an updated version of the device operating software, etc.

The visit with the practitioners therefore usually requires two different devices, as well as specific manipulations for placing the surface electrodes and collecting the ECG signals.

Moreover, the use of these two devices requires the patient to come to a specifically equipped center, usually having the consequence of routine visits that are spaced farther apart, resulting in a less rigorous follow-up of the patient.

In order to overcome such drawbacks, some algorithms for reconstructing a surface ECG based upon EGM signals (that is from the signals directly provided by the implantable device) have been developed. Indeed, the reconstruction of the surface ECG based upon EGM signals would allow:

to avoid, during routine visits, having to place surface electrodes and resort to an ECG recorder;

to therefore render the visit simpler and quicker, eventually allow performing the routine visit at the patient's home, and subsequently shorten the intervals between successive visits, and improve the patient's follow-up; and to eventually allow a remote transmission of the EGM data recorded by the implanted device, without the intervention of a practitioner or medical aid.

Various algorithms for surface ECG reconstruction based upon EGM signals have been proposed so far. U.S. Pat. No. 5,740,811 (Hedberg, et al.) proposes to synthesize a surface ECG signal by combining a plurality of EGM signals by means of a neural network and/or fuzzy logic and/or summer circuit, after learning performed by an algorithm of the "feed-forward" type. Such technique, operating through a linear unidimensional filtering, has the drawback of producing an output signal that is corresponding to only one lead of the surface ECG, and therefore only provides the practitioner with a very narrow vision of the patient's cardiac activity, compared to the usual twelve leads provided by an external ECG recorder. Another drawback of such technique is that it does not take into account the position of the endocardial leads, which may change between the moment of the learning process and that of the use of the device, a change in the heart electrical axis will have the effect of biasing the synthesized ECG signal, which will no longer be meaningful, with a risk to mask the heart disorder which may then not be diagnosed.

U.S. Pat. No. 6,980,850 (Kroll, et al.) proposes to overcome this difficulty, by proposing a method of surface ECG reconstruction implementing a matrix transform allowing to render each of the surface ECG leads individually. Such transform also allows to take into account several parameters, such as patient's respiratory activity or posture, which influence tracking the position of the endocardial leads through space. The proposed reconstruction consists of transforming, through a predetermined transfer matrix, an input vector representative of a plurality of EGM signals into a resulting vector representative of the different ECG leads. The transfer matrix is learned through averaging plural instant matrices based upon ECG and EGM vectors recorded simultaneously over a same period of time along a learning phase.

Although this technique brings an improvement to that proposed in the previous cited patent, it nevertheless presents certain drawbacks. First, it makes the assumption there exists a linear relationship between ECG and EGM vectors: such an approximation, though relatively accurate with patients presenting a regular rhythm, leads in some cases to important errors of ECG reconstruction in the presence of atypical or irregular signal morphologies—corresponding precisely to potentially pathologic cases. Moreover, the parameters of the transfer matrix are determined during a learning phase corresponding to a patient condition at a given moment. Such a situation may no longer be representative several weeks or months later, notably due to the evolution of the patient's pathology; such evolution will not be taken into account by the algorithm, except if the patient is requested to come again to a clinical center for a recalibration of the algorithm (calculation of a new transfer matrix).

Other approaches have also been proposed, such as that described in US patent application US 2005/0288600 (Zhang et al.), which consists of using, instead of EGM signals (which require the use of electrodes placed on endocardial electrodes), some subcutaneous ECG signals collected by means of a reduced number of electrodes directly placed on the surface of the implanted device's case. The ECG is then directly obtained from the inside of the patient's body instead of being obtained from surface electrodes applied on the skin, as with standard ECG recorders. The collected different subcutaneous ECG signals are split and undergo an analysis (morphology, time intervals, frequential analysis) as a function of criteria stored in a memory. The result of this analysis is compared to a reference that has been previously memorized and updated by the system, notably when some changes occur. The analysis of the signals allows to follow the evolution of the patient's heart rhythm so as to perform a cardiac diagnostic.

However, making electrodes on the surface of a case is not easy to do from a technological point of view.

OBJECTS AND SUMMARY OF THE INVENTION

It is therefore an object of the present invention to provide a way to overcome the aforementioned drawbacks, by proposing a surface ECG reconstruction of all the leads as they can be presented to a practitioner when he uses a standard ECG recorder, while taking into account the following constraints:
   parameters specific to the patient including: orientation and size of the heart, thickness of biological tissues, etc.;
   nature and evolution of the pathology;
   type of implanted device (pacemaker, defibrillator or resynchronizer, or dual, triple or quadruple-chamber device, etc.); and
   tracking of endocardial leads localization.

Moreover, the invention provides the following advantages:
   a method that is partially and totally independent of the patient,
   a reconstructed ECG close to an actual ECG,
   a method that does not require too much computing power,
   possible implementation in the implantable device, an external programmer, a home monitoring monitor or a remote data server, based upon data remotely transmitted thereto.

Broadly, the present invention is directed to a reconstruction method that is based upon a vectorial approach involving estimating the surface ECG not directly from the endocardial EGM, but by using an intermediate tridimensional vectorial representation of the various ECG or EGM signals, respectively.

More particularly, the present invention is directed to a method including the following successive steps:
   a) acquisition of a plurality of endocardial electrogram signals through a plurality of endocardial or intravascular leads (located in blood vessels of the heart), defined based upon said endocardial electrodes;
   b) calculation, through combination of the endocardial electrogram signals acquired at step a), of a corresponding endocardial vectogram;
   d) estimation, based upon the endocardial vectogram calculated at step b), of a reconstructed surface vectocardiogram; and
   e) calculation of the surface electrocardiogram signals corresponding to said reconstructed surface vectocardiogram.

Step b) of the endocardial vectogram calculation preferably may comprise an orthogonalization processing, notably requiring a Karhunen-Loeve transform.

In a preferred embodiment, a step optionally may also be added, between steps b) and d), of angular resealing the orthonormated mark of the endocardial vectogram upon that of the surface vectocardiogram. Determination of angular resealing parameters may be performed with a preliminary calibration phase through the following sub-steps:
   i) obtaining a set of reference data through simultaneous acquisition of endocardial electrogram signals and surface electrocardiogram signals;
   ii) calculation, through combination of the surface electrocardiogram signals acquired at step i), of the corresponding surface vectocardiogram;
   iii) calculation, through combination of endocardial electrogram signals acquired at step i), of the corresponding endocardial vectogram;
   iv) angular resealing of the orthonormated mark of the endocardial vectogram upon that of the surface vectocardiogram;
   v) estimation, based upon the endocardial vectogram calculated at step iii), of a reconstructed surface vectocardiogram; and
   vi) adjustment of the angular resealing parameters of step iv) so as to minimize the deviation between the surface vectocardiogram calculated at step ii) and the reconstructed surface vectocardiogram calculated at step v). Determining angular resealing parameters can preferably be implemented through an adaptive neural network.

In a preferred embodiment step d) of estimation of the reconstructed surface vectocardiogram can comprise a nonlinear filtering applied to the endocardial vectogram as calculated through step b), preferably a filtering implemented by an adaptive neural network.

The parameters of non-linear filtering can be determined during a preliminary calibration phase through the following sub-steps:
   i) obtaining a set of reference data through simultaneous acquisition of endocardial electrogram signals and surface electrocardiogram signals;
   ii) calculation, through combination of the surface electrocardiogram signals acquired at step i), of the corresponding surface vectocardiogram;
   iii) calculation, through combination of endocardial electrogram signals acquired at step i), of the corresponding endocardial vectogram;
   iv) possible angular rescaling of the orthonormated mark of the endocardial vectogram upon that of the surface vectocardiogram;

v) estimation, through applying non-linear filtering to the endocardial vectogram calculated at step iii), of a reconstructed surface vectocardiogram; and vi) adjustment of the non-linear filtering parameters of step v) so as to minimize the deviation between the surface vectocardiogram calculated at step ii) and the reconstructed surface vectocardiogram calculated at step v).

The non-linear filtering may also receive as input one parameter selected from among the group consisting of: a respiratory signal; information on the position of the endocardial sensing electrodes; a phase of the cardiac cycle, e.g., P, QRS or T; and an endocardial impedance signal, e.g., representative of a thoracic volume or respiration.

The endocardial leads used for the acquisition of endocardial electrogram signals are typically defined based upon a plurality of electrodes chosen from among the group consisting of: right ventricular distal electrode and/or right ventricular proximal electrode; right atrial distal electrode and/or right atrial proximal electrode; left ventricular distal electrode and/or left ventricular proximal electrode; ventricular or atrial defibrillation coil, and supraventricular defibrillation coil.

Another aspect of the present invention is directed towards an apparatus for reconstructing an electrocardiogram based upon electrogram signals acquired by an implantable medical device, in which the functionality of the aforementioned method steps is implemented in a microprocessor based machine having memory and control algorithms for performing the functions. In this regard, in one embodiment, one such apparatus for processing signals representative of cardiac myocardium depolarization potentials acquired by a plurality of endocardial electrodes of an active implantable medical device of the implantable pacemaker, resynchronization, cardioversion and/or defibrillation type, includes:

a) means for acquiring a plurality of endocardial electrogram signals (EGM) representative of a plurality of endocardial or intravascular leads;

b) means for calculating, based on a combination of said acquired endocardial electrogram signals (EGM), a corresponding endocardial vectogram (VGM);

c) means for estimating, based upon the calculated endocardial vectogram, a reconstructed surface vectocardiogram (VCGreconstructed); and d) means for calculating surface electrocardiogram signals (ECG) corresponding to said reconstructed surface vectocardiogram (VCGreconstructed).

Preferably, the means for calculating the endocardial vectogram (VGM) further comprises means for performing an orthogonalization process, more preferably by performing a Karhuen-Loeve transform of said combination of EGM signals. As noted in the foregoing method, the apparatus also may perform an angular resealing of the orthonormated mark of the endocardial vectogram (VGM) upon that of the surface vectocardiogram (VCG) prior to estimating said reconstructed surface vectocardiogram. Further, the apparatus may determine the parameters of the angular resealing during a preliminary step of calibration.

It should be understood that the means for performing the various functions of the apparatus of the present invention for producing the reconstructed ECG signals includes the microprocessor, associated memory, and associated software for executing software instructions to process the acquired electrogram signals and perform the reconstruction of the ECG therefrom as described herein. This results in a reconstructed ECG data which a practitioner can then utilize in the same manner for patient follow-up care as real ECG data would be used. Advantageously, it should be understood that the apparatus for producing the reconstructed ECG may be employed in any of a number of implantable medical devices, as well as in devices that are not implanted, but can acquire the EGM signal obtained from a patient, e.g., by an implanted device (or by electrodes that are at least temporarily implanted in the patient).

Yet another aspect of the present invention is directed to a software control module (instruction set) that can be installed in an implantable device or in a non-implanted device such as a patient monitor or a programmer, that can reconstruct ECG signals from acquired EGM signals, as such EGM signals may be provided by an implanted device and transmitted to such non implanted device, and stored in memory for subsequent processing. One such software control module includes:

a) a first instruction set for acquiring a plurality of endocardial electrogram signals (EGM) representative of a plurality of endocardial or intravascular leads;

b) a second instruction set for calculating, based on a combination of said acquired endocardial electrogram signals (EGM), a corresponding endocardial vectogram (VGM);

c) a third instruction set for estimating, based on the calculated endocardial vectogram, a reconstructed surface vectocardiogram (VCGreconstructed); and d) a fourth instruction set for calculating surface electrocardiogram signals (ECG) corresponding to said reconstructed surface vectocardiogram (VCGreconstructed).

Preferably, the software control module also includes an instruction set for performing an orthogonalization process, more preferably by performing a Karhuen-Loeve transform of said combination of EGM signals. The software control module also may include instructions for performing an angular resealing of the orthonormated mark of the endocardial vectogram (VGM) upon that of the surface vectocardiogram (VCG) prior to estimating said reconstructed surface vectocardiogram as described in the above mentioned method. Further, the instruction set may perform a preliminary calibration sequence for determining the parameters of the angular resealing and nonlinear filtering and an adaptive neutral network.

It should be understood that the software control module also can implement the other method steps described herein, and that a person of ordinary skill in the art could employ any of a number of specific instruction sequences to implement the control software of the present invention. Further, it should be understood that such control software can be uploaded to an existing implanted or non implantable machine that already acquires EGM signals of a patient, using conventional uploading technology, so as to be able to produce the reconstructed ECG signals in accordance with the present invention.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed, in which like reference characters refer to like elements, and in which:

FIG. 1 shows, in projection on three planes and in axonometric perspective, the loop described by a typical vectocardiogram (VCG) over a cardiac cycle;

FIG. 2 is a schematic showing the steps of the method of the present invention, allowing reconstruction of an electrocardiogram ECG based upon the electrogram (EGM) signals produced by an implantable device;

FIG. 3 shows, in projection on three planes and in axonometric perspective, the loop described by a typical vectocardiogram (VCG) over three successive cardiac cycles;

FIG. 4 is a schematic showing the steps implemented during the preliminary calibration phase, so as to define the parameters for angular resealing to be applied to the VGM;

FIG. 5 is a schematic showing the steps implemented during the preliminary calibration phase, so as to define the parameters for the non-linear vectorial filtering allowing to reconstruct the VCG based upon rescaled VGM.

DETAILED DESCRIPTION OF THE INVENTION

Figure 6:
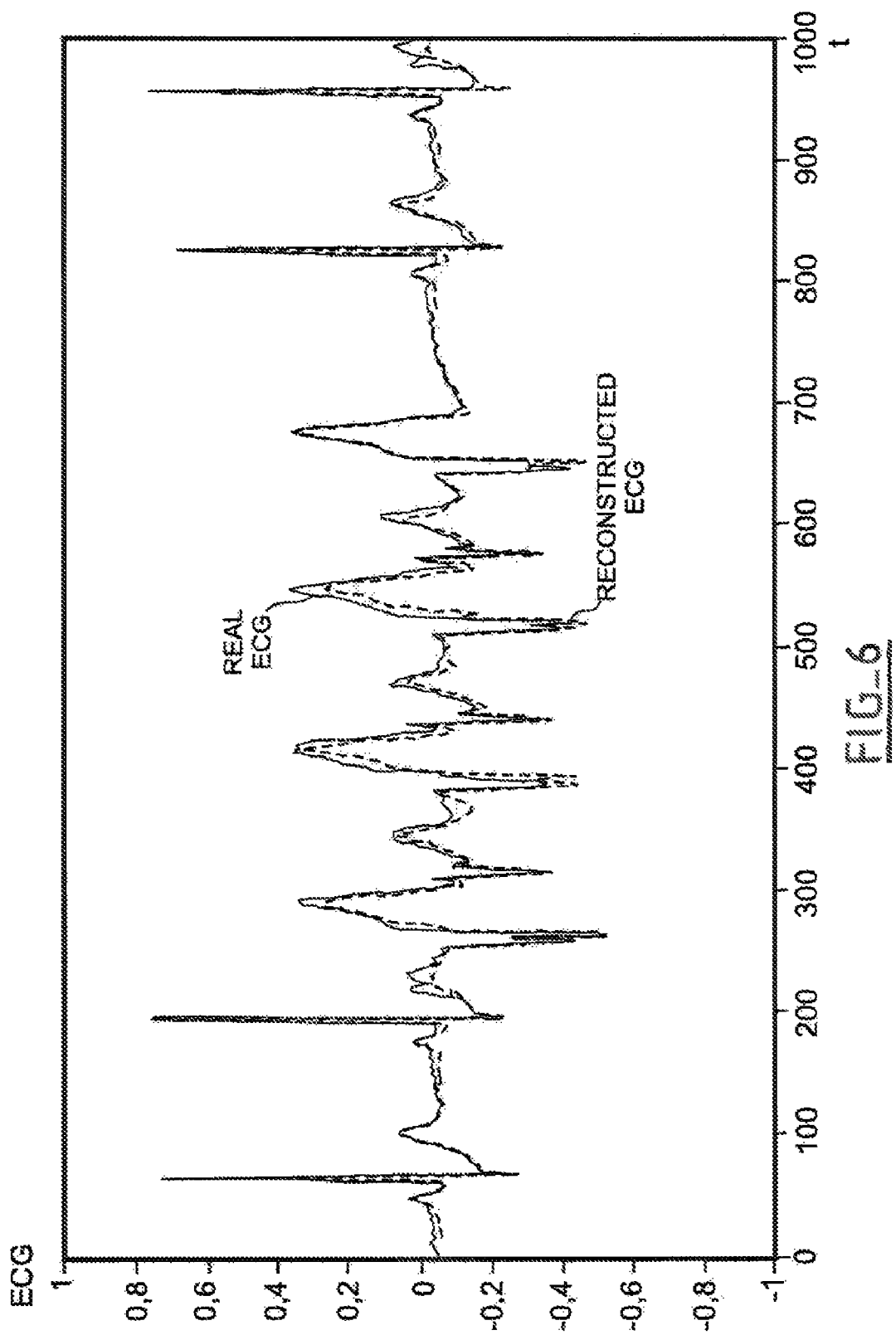
FIG. 6 is a comparative example showing the aspect of the reconstructed ECG based upon the EGM signals through implementing the present invention, comparing to an actual ECG collected by means of surface electrodes following a conventional technique.

With reference to FIGS. 1-6, one will now describe a preferred embodiment of a device employing the method, apparatus, and software control module in accordance with the present invention. Regarding the software-related aspects thereof, the functionality and processes of the present invention can be implemented by an appropriate programming of the software of a known implantable pulse generator, for example, a pacemaker or defibrillator/cardioverter, comprising means for acquiring a signal provided through endocardial leads.

The invention can preferably be applied to the commercial implantable devices marketed by ELA Medical, Montrouge France, such as Symphony and ELA Rhapsody brand pacemakers and comparable commercial and/or proprietary devices of other manufacturers. These devices are equipped with programmable microprocessors, including circuits intended to acquire, format and process electrical signals collected by implanted electrodes and various sensors, and deliver pacing pulses to implanted electrodes. It is also possible to upload towards these devices, by telemetry, pieces of software (i.e., a software control module) that will be stored in internal memory and run so as to implement the features and functionality of the invention, as described herein. Implementing the features of the invention into these devices is believed to be easily feasible by a person of ordinary skill in the art, and will therefore not be described in detail in this document.

The present invention can however be implemented not only within an implantable device (direct processing of the VGM signals), but also within an external programmer used by a practitioner, so as to download and analyze the heart signals collected and memorized by an implantable device. In a preferred embodiment, the present invention is also implemented in a home monitoring monitor, which is a particular type of external programmer, the operation of which is typically totally automated and does not require the intervention of a practitioner, notably to allow remote transmission towards a distant site at regular intervals, for example, on a daily basis, of the collected data, for further analysis and patient follow-up. The present invention can equally be implemented level with the data server of said distant remote site, the raw EGM data thus being directly uploaded towards this server, with no preliminary processing and stored in memory therein. The processing can then be performed by the server or terminal (PC or programmer) connected thereto.

In a general manner, cardiac electrical activity is manifesting itself on the surface of the patient's body through signals that are said to be electrocardiographic (ECG), that are collected between two pairs of electrodes applied on determined locations on the patient's thorax, each pair of electrodes determining a vector. The whole constitutes a set of twelve vectors, in such a way that cardiac electrical activity can be assimilated to twelve-dimensional representation that is varying in time. The bipolar leads (I, II, III) and unipolar leads (aVF, aVR, aVL) allow to represent the electrical activity in the frontal plane, while precordial leads (v1 to v6) represent the electrical activity in the horizontal plane.

The surface electrical activity can also be represented in a tridimensional graphical format by a vector in coordinates x, y, z as it has been proposed by E. Frank, An Accurate, Clinically Practical System for Spatial Vectocardiography, *Circulation*, 13:737-749, May 1956. Such a representation, called vectocardiogram (VCG), can be obtained from a set of seven surface electrodes, and contains all the information on the myocardium depolarization and repolarization processes, that is to say it is as much complete, in terms of information, as the twelve unidimensional ECG signals.

The VCG is thus presented as a vector, the module and direction of which (by reference to the bench mark defined by the patient's thorax) being constantly varying in time. The tip of this vector, at each heart beat, is describing a loop that is visually representing the patient's cardiac activity. FIG. 1 shows an example of such a loop described by the tip of the VCG vector along one cardiac cycle. The VCG loop is represented in perspective (FIG. 1*a*) and in projection onto three planes, respectively frontal, horizontal and sagittal (FIGS. 1*b* to 1*d*).

It has also been demonstrated, as notably described in U.S. Pat. No. 4,850,370 (Dower), that it is possible to reduce the system of Frank, which used to comprise seven electrodes, to a system with only four electrodes, called EASI system. Two transform matrices have also been defined, called "Dower matrix" and "inverse Dower matrix", allowing the retrieval of the twelve ECG leads (unidimensional signals) based upon the VCG, and conversely. In other words, this document describes a biunivocal transform between a plurality (twelve) of ECG signals merely defined in the time domain, and the variations within that same time domain, of the tridimensional and vectorial graphical representation of the vectocardiogram (VCG).

The basic idea behind the present invention is the reconstructing the surface ECG lead signals starting from the endocardial EGM signals collected by the implanted device, through an intermediate vectorial transform implying a reconstruction of the VCG. Essentially, one aspect of the present invention is directed to a method for:

collecting the endocardial electrogram (EGM) signals,
constructing the corresponding vectogram (VGM),
transforming said vectogram (VGM) into a vectocardiogram (VCG), and
reconstructing the surface electrogram (ECG) signals based upon the VCG by means of an inverse Dower matrix (or any other technique leading to similar results).

These different steps are shown on the schematics of FIG. 2, with the following successive steps:

Step 10: selection of the EGM electrodes of the implant allowing for collection the EGM signals that will allow construction of a corresponding endocardial vectogram, Step 12: construction of the endocardial vectogram VGM, tridimensional representation of the cardiac vector based upon the electrogram (EGM) signals. The vectogram VGM has three orthogonal components providing the propagation of cardiac activity in three planes x, y, z and its components are calculated by an orthogonalization, by using for example a Karhunen-Loeve transform (see below).

Step 14: construction of a resealed vectogram VGMrescaled, through a rotation $M(\theta)$ of the vectogram providing VGMrescaled=$M(\theta) \cdot$VGM, so as to make the orthonormalized mark of the resealed vectogram VGMrescaled, to that of the vectocardiogram.

Step 16: estimation of the reconstructed vectocardiogram VCGreconstructed based upon the resealed vectogram, with VCGreconstructed =$W \cdot$VGMrescaled.

Step 18: calculation of the twelve ECG vectors through applying the inverse Dower matrix D, with ECG=$D \cdot$VCGreconstructed.

Each of these steps will be described in more detail. below.

The purpose is to acquire a plurality of endocardial EGM signals based upon a corresponding plurality of leads corresponding to pairs of endocardial electrodes connected to the implanted device's case.

The choice for the electrodes constituting these leads depends upon the type of implanted device to be considered: pacemaker (for the treatment of bradycardiae), defibrillator (for the treatment of tachycardiae and fibrillations) or resynchronization device (for the treatment of heart failure). Further, three pacing modes are distinguished: single, dual or triple-chamber. To these different features are corresponding different electrodes, and a different number of EGM signals according thereto.

If "RV", "RA" and "LV" respectively stand for the right ventricular, right atrium and left ventricular electrodes of the endocardial leads, with "+" or "−" indicating the respective distal or proximal locations of the electrode, and "CoilV" and "SVC" stand for the electrodes for ventricular and supraventricular fibrillation respectively, then the possible electrode combinations are the following (with, for each of them, the possibility to define a lead between the two electrodes, or between one of them and the implantable pulse generator case):

single chamber: RV+, RV− (and CoilV in the case of a defibrillator); a single chamber pulse generator can thus provide two EGM signals thanks to the distal and proximal electrodes, the ground being corresponding to the case. The "defibrillator" version can provide three EGM signals, thanks to the additional CoilV electrode.

dual chamber: RV+, RV−, RA+, RA− (and CoilV and SVC in the case of a defibrillator); a dual-chamber pulse generator can thus provide four EGM signals, and six in the case of a defibrillator.

triple chamber: RV+, RV−, RA+, RA−, LV+, LV− (and CoilV and SVC in the case of a defibrillator); a triple-chamber pulse generator can thus provide six EGM signals, and eight in the case of a defibrillator.

The present invention is preferably implemented in dual-chamber or triple-chamber implantable devices, so as to allow recording the electrical depolarization in the three dimensions, preferably by including among the selected EGM signals, the RV unipolar lead and the unipolar and bipolar RA leads.

The present invention is preferably implemented in dual-chamber or triple-chamber implantable devices, so as to allow recording the electrical depolarization in the three dimensions, preferably by including among the selected EGM signals, the RV unipolar derivation and the unipolar and bipolar RA derivations.

Construction of the Vectogram VGM

The purpose of this step (step 12 in FIG. 2) is to construct an orthogonal basis based upon a set of electrogram signals.

For the implementation of this invention, it is preferable to use, among different possible algorithms, the discrete Karhunen-Loeve transform (KLT).

The principle of Karhunen-Loeve algorithm is as follows:

Let $X_{EGM}$ be the matrix whose N components $EGM_1$ to $EGM_N$ are the electrogram vectors corresponding to the isolated beats collected through the endocardial electrodes (for a better legibility, the temporal factor t is on purpose not referred to here).

The $EGM_i$ signals are normalized based upon the signal with the highest energy and of a duration approximately equal to that of the wave to be reconstructed.

One can then define the real and symmetric covariance matrix $C_{X_{EGM}X_{EGM}}$, that is:

$$C_{X_{EGM}X_{EGM}} = E(X_{EGM}X_{EGM}^T)$$

And its associated matrix of eigenvectors A such as:

$$C_{X_{EGM}X_{EGM}}A = \Lambda A,$$

Where the matrix $M(\theta)$ is constituted of the N eigenvalues $\lambda_i$ of $C_{X_{EGM}X_{EGM}}$.

The transform given by:

$$Y = AX_{EGM} = [Y_1 \ldots Y_i \ldots Y_N]^T$$

is called the discrete Karhunen-Loeve transform (KLT). Its covariance matrix CYY is:

$$C_{YY} = E(YY^T) = E(AX_{EGM}X_{EGM}^T A^T) = AC_{X_{EGM}X_{EGM}}A^T$$

The CYY matrix has therefore the same eigenvalues as the $C_{X_{EGM}X_{EGM}}$ matrix, and the Yi vectors are represented in an orthogonal mark whose axes are the principal axes of the EGMi vectors (the eigenvectors of $C_{X_{EGM}X_{EGM}}$) and constitute the reconstructed vectogram, hereinafter referred to as VGM.

Experimentation has shown that when applying a Karhunen-Loeve transform to all collected EGM signals, three components contain more than 90% of the information. It is then observed that the estimated VGM has the aspect of an ellipse in the space of the three principal components. FIG. 3 shows an example of VGM thus reconstructed, for three successive heartbeats. In this figure, the VCG loop is represented in perspective (FIG. 3a) and in projection on the three principal planes (FIGS. 3b to 3d), directions of which are determined by a principal component analysis algorithm.

Angular adjustments shall however be performed so that the axes of the vectogram vectors and that of the vectocardiogram have the same supports. That requires to proceed (step 14 of FIG. 2) to the rotation of the basis formed by the principal components of the vectogram VGM.

If the three angles $\theta x$, $\theta y$ and $\theta z$ are known, then the resealed vectogram VGMrescaled can be calculated as:

$$VGMrescaled = M(\theta) \cdot VGM$$

Where the rotation matrix $M(\theta)$ is defined by:

$$M(\Theta) = M_x(\theta_x) \cdot M_y(\theta_y) \cdot M_z(\theta_z)$$

with:

$$M_x(\theta_x) = \begin{bmatrix} 1 & 0 & 0 \\ 0 & \cos(\theta_x) & -\sin(\theta_x) \\ 0 & \sin(\theta_x) & \cos(\theta_x) \end{bmatrix}$$

$$M_Y(\theta_Y) = \begin{bmatrix} 0 & 1 & 0 \\ -\sin(\theta_y) & 0 & \cos(\theta_y) \\ -\sin(\theta_y) & 0 & \cos(\theta_y) \end{bmatrix}$$

$$M_Z(\theta_Z) = \begin{bmatrix} \cos(\theta_z) & -\sin(\theta_z) & 0 \\ \sin(\theta_z) & \cos(\theta_z) & 0 \\ 0 & 0 & 1 \end{bmatrix}$$

On a practical point of view, the three angles θx, θy and θz are unknown. They have to be learned through a learning basis constituted of EGM electrograms and ECG electrocardiograms acquired simultaneously at the moment of the implantation. FIG. 4 shows the different steps of this preliminary learning phase allowing to define the parameters of the angular rescaling.

The first step consists of simultaneously acquiring the corresponding EGM and ECG signals (step 20). The EGM signals are utilized to reconstruct a corresponding VCG ($VCG_{reconstructed}$), reconstructed through the steps 22, 24 and 26 which are similar to the steps 12, 14 and 16 described above in reference to FIG. 2.

In parallel, the ECG signals are processed (step 28) through a Dower transform, or similar transform allowing to produce the corresponding VCG ($VCG_{real}$) directly coming from collected ECG signals.

The two VCG (real and reconstructed) are then correlated, and the angles θx, θy and θz estimated so as to minimize, through least squares fitting, the mean-square error $\epsilon^2$:

$$\varepsilon^2 = \min_{M,\tau} \|VCG - M(\Theta) \cdot VGM_r \cdot J_\tau\|^2$$

Where $J_\tau$ allows to preserve the temporal synchronizing of the vectocardiographic loops.

Estimation of the Vectocardiogram VCG

The reconstructed VCG $VCG_{reconstructed}$ can then be calculated (step 16 of FIG. 2) through transforming the rescaled VGM ($VGM_{rescaled}$), preferably through applying a non-linear vectorial filtering, that is:

$$VCG_{reconstructed} = [VCG_{recx} \quad VCG_{recy} \quad VCG_{recz}]^T$$
$$= W \cdot VGM_{rescaled}$$

Or:

$$VCG_{reconstructed} = [VCG_{recx} \quad VCG_{recy} \quad VCG_{recz}]^T$$
$$= \begin{bmatrix} W_X & 0 & 0 \\ 0 & W_Y & 0 \\ 0 & 0 & W_Z \end{bmatrix} \cdot [VGM_{recx} \quad VGM_{recy} \quad VGM_{recz}]^T$$

The matrix W can be approximated by a neural network, for example of the same type as that described in U.S. Pat. No. 5,740,811 (Hedberg et al.) cited above. This neural network is parameterized during the same learning phase as that which served for determining the parameters of angular resealing to be applied to the VGM.

A neural network, for example, of the "spiking" type, can perform the features represented in 24 and 26, after a learning trying to minimize through least squares fitting, the mean-square error $\epsilon^2$. Such a network is for instance described by Rom et al., *Adaptative Cardiac Resynchronization Therapy Device Based on Spiking Neurons Architecture with Reinforcement Learning Scheme, Classical Conditioning and Synaptic Plasticity*, PACE 2005; 28: 1168-1173, November 2005.

This parameterizing is shown by FIG. 5. The first step consists of simultaneously collecting the corresponding EGM and ECG signals (step 30).

The EGM signals are utilized to reconstruct a corresponding VCG ($VCG_{reconstructed}$), reconstructed through the steps 32, 34 and 36 which are similar to the steps 12, 14 and 16 described above in reference to FIG. 2.

In parallel, the ECG signals are processed (step 38) through a Dower transform, or similar transform allowing to produce the corresponding VCG ($VCG_{real}$) directly coming from collected ECG signals.

The two VCG (real and reconstructed) are then correlated, and the filtering parameters 36 are estimated so as to minimize, through least squares fitting, the mean-square error.

After this learning phase, the matrices M(θ) and W are fixed, but may also be updated by the practitioner if he wishes.

A neural network, for example of the "spiking" type, can equally perform the features represented in 34 and 36, after a learning trying to minimize through least squares fitting, the mean-square error $\epsilon^2$.

Estimation of the ECG Signals B8

The twelve leads of the surface ECG ECGreconstructed are estimated (step 18 of FIG. 2) following the principle defined by Dower, that is by applying the inverse Dower matrix D such as:

ECGreconstructed=D·VCGreconstructed.

FIG. 6 provides a superimposed representation of an example of ECG reconstructed based upon EGM signals by utilizing a neural network according to the present invention, compared to the real ECG directly collected by electrodes placed on the patient's body.

ECG reconstruction through the method of the present invention allows a very good approximation of the real ECG, even for heartbeats with very different morphologies, which makes a difference when comparing notably to the existing techniques of ECG reconstruction by linear filtering such as those proposed by U.S. Pat. No. 6,980,850 (Kroll et al.) cited above, which leads to unsatisfactory results in the case of atypical morphologies of the cardiac signal.

The ECG reconstruction method following the present invention can be applied, if need be, separately and independently to the P, QRS and T waves of the cardiac signal, so as to allow a specific analysis.

Finally, as shown in FIG. 2 by phantom line arrows leading to block 16, the vectorial filtering allowing to reconstruct the VCG based upon the VGM can receive as input, some additional parameters likely to modify the electrical propagation of the cardiac activity between the myocardium and the patient's body surface, such as: position of the electrodes, phase of the respiratory cycle, and/or variation of the thoracic volume (for example measured by a transthoracic impedance measurement).

Although the detailed description of the invention has been discussed in the context of a method, it should be understood that the present invention applies equally to an apparatus and to a software control module that operates on EGM data to perform the functionality of the method steps to obtain reconstructed ECG data. Indeed, one skilled in the art will appreciate that the present invention can be practical by other than the embodiments described herein, which are presented for purposes of illustration and not of limitation.

We claim:

1. A process for processing signals representative of cardiac myocardium depolarization potentials, said signals being collected by a plurality of endocardial electrodes of an active implantable medical device such as an implantable pacemaker, device for resynchronization, cardioversion and/or defibrillation, the process being performed by one of: the active implantable medical device, an external programmer, data server, the process comprising the steps of:
- a) acquiring a plurality of endocardial electrogram signals (EGM) through a plurality of leads, each lead of the plurality of leads being collected between at least two pairs of endocardial electrodes selected from the plurality of endocardial electrodes;
- b) calculating, through a combination of the plurality of endocardial electrogram signals (FGM) acquired at step a), a corresponding endocardial vectogram (VGM);
- d) estimating, based upon the endocardial vectogram calculated at step b), a reconstructed surface vectocardiogram (VCGreconstructed); and
- e) reconstructing surface electrocardiogram signals (ECG) corresponding to said reconstructed surface vectocardiogram (VCGreconstructed).

2. The process of claim 1, wherein step b) of calculating the endocardial vectogram (VGM) further comprises performing an orthogonalization process.

3. The process of claim 2, wherein performing said orthogonalization process further comprises performing a Karhuen-Loeve transform of said combination of EGM signals.

4. The process of claim 1, further comprising, between steps b) and d):
- c) angular rescaling the orthonormalized mark of the endocardial vectogram (VGM) upon that of the surface vectocardiogram (VCG).

5. The process of claim 4, further comprising a preliminary step of calibration comprising determining parameters of said angular rescaling.

6. The process of claim 5, wherein determining angular rescaling parameters further comprising the steps of:
- i) obtaining a set of reference data through simultaneous acquisition of endocardial electrogram signals (EGM) and surface electrocardiogram signals (ECG);
- ii) calculating, through a combination of the surface electrocardiogram signals (ECG) acquired at step i), a corresponding surface vectocardiogram (VCGreal);
- iii) calculating, through a combination of endocardial electrogram signals (EGM) acquired at step i), a corresponding endocardial vectogram (VGM);
- iv) angular rescaling the orthonormalized mark of the endocardial vectogram (VGM) upon that of the surface vectocardiogram (VCGreal);
- v) estimating, based upon the endocardial vectogram (VGM) calculated at step iii), of a reconstructed surface vectocardiogram (VCGreconstructed); and
- vi) adjusting the angular rescaling parameters of step iv) so as to minimize a deviation between the surface vectocardiogram (VCGreal) calculated at step ii) and the reconstructed surface vectocardiogram (VCGreconstructed) calculated at step v).

7. The process of claim 6, wherein said deviation to be minimized is the root-mean-square deviation.

8. The process of claim 6, further comprising providing an adaptive neural network for a determination of said angular rescaling parameters.

9. The process of claim 1, wherein, the step d) of estimating the reconstructed surface vectocardiogram (VCGreconstructed) further comprises applying a non-linear filtering to the endocardial vectogram calculated at step b).

10. The process of claim 9, further comprising providing an adaptive neural network to implement said non-linear filtering, 11. The process of claim 9, further comprising a preliminary calibration step comprising determining parameters of said non-linear filtering.

12. The process of claim 11, wherein determining non linear filtering parameters further comprising the steps of:
- i) obtaining a set of reference data through simultaneous acquisition of endocardial electrogram signals (EGM) and surface electrocardiogram signals (ECG);
- ii) calculating, through a combination of the surface electrocardiogram signals (ECG) acquired at step i), a corresponding surface vectocardiogram (VCGreal);
- iii) calculating, through combination of endocardial electrogram signals (EGM) acquired at step i), a corresponding endocardial vectogram (VGM);
- iv) conducting a possible angular rescaling of an orthonormalized mark of the endocardial vectogram (VGM) upon that of the surface vectocardiogram (VCGreal);
- v) estimating, through applying non-linear filtering to the endocardial vectogram calculated at step iii), a reconstructed surface vectocardiogram (VCGreconstructed); and
- vi) adjusting the non-linear filtering parameters of step v) so as to minimize a deviation between the surface vectocardiogram (VCGreal) calculated at step ii) and the reconstructed surface vectocardiogram (VCGreconstructed) calculated at step v).

13. The process of claim 9, further comprising providing to said non-linear filtering as an input, at least one parameter selected from among: at respiratory signal, information on the position of the endocardial sensing electrodes, the P, QRS or T phase of the cardiac cycle; and a signal representative of intracardiac impedance.

14. The process of claim 1, wherein said intracardiac signals are collected using at least one of: right ventricular distal and/or proximal electrode, right atrial distal and/or proximal electrode, left ventricular distal and/or proximal electrode, ventricular or atrial defibrillation coil, and supra-ventricular defibrillation coil.

15. The process of claim 1, wherein the plurality of endocardial electrodes of the active implantable medical device comprises two to four endocardial electrodes implanted to a patient.

16. Apparatus for processing signals representative of cardiac myocardium depolarization potentials, comprising:
- a) means for acquiring a plurality of endocardial electrogram signals (EGM) representative of a plurality of leads;
- b) means for calculating, based on a combination of said acquired plurality of endocardial electrogram signals (EGM), a corresponding endocardial vectogram (VGM);
- c) means for estimating, based upon the calculated endocardial vectogram, a reconstructed surface vectocardiogram (VCGreconstructed); and
- d) means for calculating surface electrocardiogram signals (ECG) corresponding to said reconstructed surface vectocardiogram (VCGreconstructed).

17. The apparatus of claim 16, wherein said means for calculating the endocardial vectogram (VGM) further comprises means for performing an orthogonalization process.

18. The apparatus of claim 17, wherein said means for performing said orthogonalization process further comprises means for performing a Karhuen-Loeve transform of said combination of EGM signals.

19. The apparatus of claim 16, further comprising:
means for angular rescaling an orthonormalized mark of the endocardial vectogram (VGM) upon that of the surface vectocardiogram (VCG) prior to estimating said reconstructed surface vectocardiogram.

20. The apparatus of claim 19, further comprising means for determining parameters of said angular rescaling during a preliminary calibration.

21. The apparatus of claim 16, wherein, the means for, estimating the reconstructed surface vectocardiogram (VCGreconstructed) further comprises means for applying a non-linear filtering to the calculated endocardial vectogram, said means for nonlinear filtering further comprising a neural network.

22. The apparatus of claim 16, wherein the plurality of endocardial electrodes of the active implantable medical device comprises two to four endocardial electrodes implanted to a patient.

23. A non-transitory software control module for processing signals representative of cardiac myocardium depolarization potentials, comprising:
   a) a first instruction set for acquiring a plurality of endocardial electrogram signals (EGM) representative of a plurality of leads;
   b) a second instruction set for calculating, based on a combination of said acquired endocardial electrogram signals (EGM), a corresponding endocardial vectogram (VGM);
   c) a third instruction set for estimating, based upon the calculated endocardial vectogram, a reconstructed surface vectocardiogram (VCGreconstructed); and
   d) a fourth instruction set for calculating surface electrocardiogram signals (ECG) corresponding to said reconstructed surface vectocardiogram (VCGreconstructed).

24. The non-transitory software control module of claim 23, wherein said second instruction set further comprises instructions performing an orthogonalization process by performing a Karhuen-Loeve transform of said combination of EGM signals.

25. The non-transitory software control module of claim 23, further comprising:
an instruction set for angular rescaling an orthonormalized mark of the endocardial vectogram (VGM) upon that of the surface vectocardiogram (VCG) prior to estimating said reconstructed surface vectocardiogram.

26. The non-transitory software control module of claim 23, further comprising an instruction set for determining parameters of said angular rescaling during a preliminary calibration.

27. The non-transitory software control module of claim 26, wherein the instruction set for determining angular rescaling parameters further comprise instructions for:
   i) obtaining a set of reference data through simultaneous acquisition of endocardial electrogram signals (EGM) and surface electrocardiogram signals (ECG);
   ii) calculating, through a combination of the surface electrocardiogram signals (ECG) acquired at step i), a corresponding surface vectocardiogram (VCGreal);
   iii) calculating, through a combination of endocardial electrogram signals (EGM) acquired at step i), a corresponding endocardial vectogram (VGM);
   iv) angular rescaling the orthonormalized mark of the endocardial vectogram (VGM) upon that of the surface vectocardiogram (VCGreal);
   v) estimating, based upon the endocardial vectogram (VGM) calculated at step iii), of a reconstructed surface vectocardiogram (VCGreconstructed); and
   vi) adjusting the angular rescaling parameters of step iv) so as to minimize the deviation between the surface vectocardiogram (VCGreal) calculated at step ii) and the reconstructed surface vectocardiogram (VCGreconstructed) calculated at step v).

28. The non-transitory software module of claim 23, wherein the plurality of endocardial electrodes of the active implantable medical device comprises two to four endocardial electrodes implanted to a patient.

* * * * *